United States Patent [19]

Klein et al.

[11] Patent Number: 4,952,562
[45] Date of Patent: Aug. 28, 1990

[54] ANTI-THROMBOTIC PEPTIDES AND PSEUDOPEPTIDES

[75] Inventors: Scott I. Klein, Audubon; Bruce F. Molino, Hatfield; Mark Czekaj, Holland; Charles J. Gardner, Royersford; Jeffrey C. Pelletier, Lansdale, all of Pa.

[73] Assignee: Rorer Pharmaceutical Corporation, Fort Washington, Pa.

[21] Appl. No.: 415,006

[22] Filed: Sep. 29, 1989

[51] Int. Cl.$^5$ .............................................. A61K 37/00
[52] U.S. Cl. .................................... 514/18; 530/330; 530/331
[58] Field of Search .................. 514/18; 530/331, 330

[56] References Cited

U.S. PATENT DOCUMENTS 4,683,291 7/1987 Zimmerman et al. .
4,857,508 8/1989 Adams et al. .......................... 514/18

FOREIGN PATENT DOCUMENTS 0319506 12/1988 European Pat. Off. .
2608160 12/1986 France .

OTHER PUBLICATIONS

"Inhibition of Platelet Adhesion to Fibronecin, Fibrinogen and von Willebrand Factor Substrates by a Synthetic Tetrapeptide Derived from the Cell-Binding Domain of Fibronection", Blood, vol. 66, No. 4 (Oct.), 1985, pp. 946-952, Haverstick et al.
"Inhibition of Fibrinogen Binding to Human Platelets by the Tetrapeptide Glycyl-L-Prolyl-L-Arginyl-L-Proline", Proc. Natl. Acad. Sci. vol. 79, (Jun.) 1982, pp. 3711-3715; Plow et al.
"The Effect of Arg-Gly-Asp-Containing Peptides on Fibrinogen and von Willebrand Factor Binding to Platelets", Proc. Natl. Acad. Sci., vol. 82 (Dec.) 1985, pp. 8057-8061; Plow et al.
"Competition for Related but Nonidentical Binding Sites on the Glycoprotein IIb-IIIa Complex by Peptides Derived from Platelet Adhesive Proteins", Cell, vol. 48, (Mar.) 1987, pp. 867-873, Santoro et al.
Plow et al., "The Effect of Arg-Gly-Asp . . . ", Natl. Acad. Sci. 12/85, pp. 8057-8061.

*Primary Examiner*—Lester L. Lee
*Assistant Examiner*—Stephen Maebius
*Attorney, Agent, or Firm*—Imre (Jim) Balogh; James A. Nicholson; Herbert H. Jervis

[57] ABSTRACT

Disclosed are novel peptides and pseudopeptides and pharmaceutical compositions thereof that inhibit platelet aggregation and thrombus formation in mammalian blood.

12 Claims, No Drawings

ANTI-THROMBOTIC PEPTIDES AND PSEUDOPEPTIDES

BACKGROUND OF THE INVENTION

1. Field of the Invention

This invention relates to novel compounds having anti-thrombotic activity. More particularly, the invention relates to novel peptides and pseudopeptides that inhibit platelet aggregation and thrombus formation in mammalian blood thereby being useful in the prevention and treatment of thrombosis associated with certain disease states, such as, myocardial infarction, stroke, peripheral arterial disease and disseminated intravascular coagulation.

2. Description of the Prior Art

Haemostasis, the biochemistry of blood coagulation, is an extremely complex and as yet not completely understood phenomena whereby normal whole blood and body tissue spontaneously arrest bleeding from injured blood vessels. Effective haemostasis requires the combined activity of vascular, platelet and plasma factors as well as a controlling mechanism to prevent excessive clotting. Defects, deficiencies, or excesses of any of these components can lead to hemorrhagic or thrombotic consequences.

Platelet adhesion, spreading and aggregation on extracellular matrices are central events in thrombus formation. These events are mediated by a family of platelet adhesive glycoproteins, i.e., fibrinogen, fibronectin, and von Willebrand factor. Fibrinogen is a co-factor for platelet aggregation, fibronectin supports platelet attachments and spreading reactions, and von Willebrand factor is important in platelet attachment to and spreading on subendothelial matrices. The binding sites for fibrinogen, fibronectin and von Willebrand factor have been located on the platelet membrane glycoprotein complex IIb/IIIa.

Adhesive glycoprotein, like fibrinogen, do not bind with normal resting platelets. However, when a platelet is activated with an agonist such as thrombin or adenosine diphosphate, the platelet changes its shape, perhaps making the GPIIb/IIIa binding site accessible to fibrinogen. The novel molecules described in this invention may block the fibrinogen receptor, thus inhibiting platelet aggregation and subsequent thrombus formation. Pharmaceutical agents and/or compositions possessing such an inhibiting effect may be provided for the prophylaxis and treatment of thrombogenic diseases, such as myocardial infarction, stroke, peripheral arterial disease and disseminated intravascular coagulation.

It has been observed that the presence of Arg-Gly-Asp (RGD) is necessary in fibrinogen, fibronectin and von Willebrand factor for their interaction with the cell surface receptor (Ruoslahti E., Pierschbacher, Cell 1986, 44, 517–18). Two other amino acid sequences also seem to take part in the platelet attachment function of fibrinogen, namely, the Gly-Pro-Arg sequence, and the dodecapeptide, His-His-Leu-Gly-Gly-Ala-Lys-Gln-Ala-Gly-Asp-Val sequence, small synthetic peptides containing the RGD or dodecapeptide have been shown to bind to the platelet GPIIb/IIIa receptor and competitively inhibit binding of fibrinogen, fibronectin and von Willebrand factor as well as inhibit aggregation of activated platelets (Plow et al. Proc. Natl. Acad. Sci. USA 1985, 82, 8057–61; Ruggeri et al. Proc. Natl. Acad. Sci. USA 1986, 5708–12; Ginsberg et al. J. Biol. Chem. 1985, 260, 3931–36; and Gartner et al. J. Biol. Chem. 1987, 260, 11,891–94).

The present invention is directed to novel peptides and pseudopeptides which inhibit platelet aggregation and subsequent thrombus formation.

SUMMARY OF THE INVENTION

In accordance with the present invention, novel peptides and pseudopeptides are provided for the prophylaxis and/or treatment of thrombotic disease states having the general formulae:

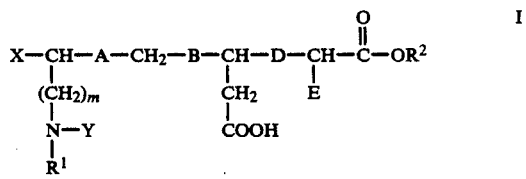

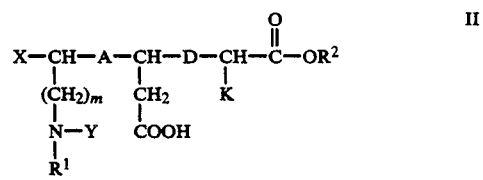

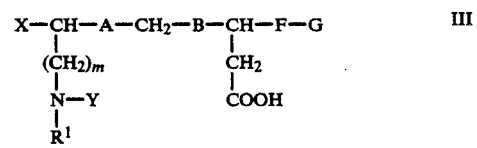

and pharmaceutically acceptable salts thereof, wherein:

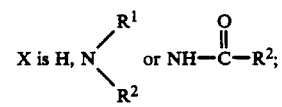

A, B and D are independently $\overset{O}{\underset{\|}{C}}-NR^2$, $CH_2O$, or $CH_2-NR^2$;

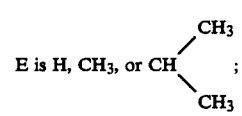

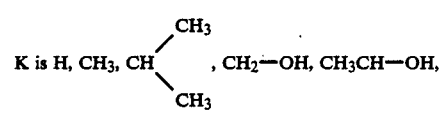

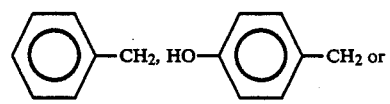

-continued

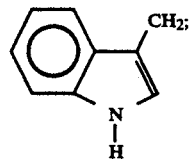

F is O or CH₂;

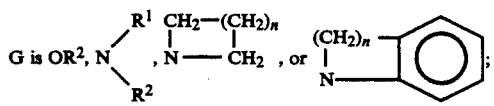

R¹ and R² are independently:

H, alkyl, cycloalkyl, aryl, and aralkyl;

m is 2-8 and n is 0-5;

provided that, in formula I, when X is NH₂, then:

m is 3, $$Y \text{ is } \underset{\underset{NH}{\|}}{C}-NH_2,$$

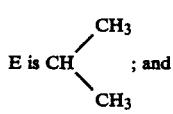

$$\text{that at least one radical in A, B and D is not } \overset{O}{\underset{\|}{C}}-NH; \text{ and}$$

provided further that, in formula III, when X is NH₂ then:

$$Y \text{ is } \overset{NH}{\underset{\|}{C}}-NH_2,$$

m is 3, $$F \text{ is } \overset{O}{\underset{\|}{C}},$$

G is OH; and $$\text{that one radical in A and B is not } \overset{O}{\underset{\|}{C}}-NH.$$

As used herein: alkyl alone and in aralkyl represent straight-chain or branched alkyl with up to 10 carbon atoms and preferably up to 6 carbon atoms; cycloalkyl means a saturated monocyclic hydrocarbon ring having 3 to about 7 carbon atoms such as cyclopropyl, cyclohexyl and the like; aryl preferably denotes phenyl or naphthyl; the aryl and aralkyl groups may carry substituents such as halo, CF₃, OR and SR wherein R denotes H or lower alkyl having 1 to 6 carbon atoms.

DETAILED DESCRIPTION OF THE INVENTION

In accordance with the present invention, novel compounds are provided which inhibit platelet aggregation by inhibiting fibrinogen binding to activated platelets and other adhesive glycoproteins involved in platelet aggregation and blood clotting. Compounds of the present invention, as tested by methods predictive of antithrombotic activity, are believed to be useful in the prevention and treatment of thrombosis associated with certain diseased states, such as myocardial infarction, stroke, peripheral arterial disease and disseminated intravascular coagulation.

The present compounds may also be useful for the treatment of certain Cancerous diseases since they may interfere with adhesive interactions between cancer cells and the extracellular matrix (Journ. of Biol. Chem., Vol. 262, No. 36 1987, pp. 17703-17711; Science, Vol. 233, 1986, pp. 467-470; and Cell, Vol. 57, 59-69, April 1989).

The compounds of the present invention may be readily prepared by standard solid phase or solution phase peptide synthesis using starting materials and/or readily available intermediates from chemical supply companies such as Aldrich or Sigma, (H. Paulsen, G. Merz, V. Weichart, "Solid-Phase Synthesis of O-Glycopeptide Sequences", Angew. Chem. Int. Ed. Engl. 27 (1988); H. Mergler, R. Tanner, J. Gosteli, and P. Grogg, "Peptide Synthesis by a Combination of Solid-Phase and Solution Methods I: A New Very Acid-Labile Anchor Group for the Solid-Phase Synthesis of Fully Protected Fragments", Tetrahedron letters 29, 4005 (1988); Merrifield, R.B., "Solid Phase Peptide Synthesis after 25 Years: The Design and Synthesis of Antagonists of Glucagon", Makromol. Chem. Macromol. Symp. 19, 31 (1988)).

We prefer to use the solid phase method schematically represented as follows:

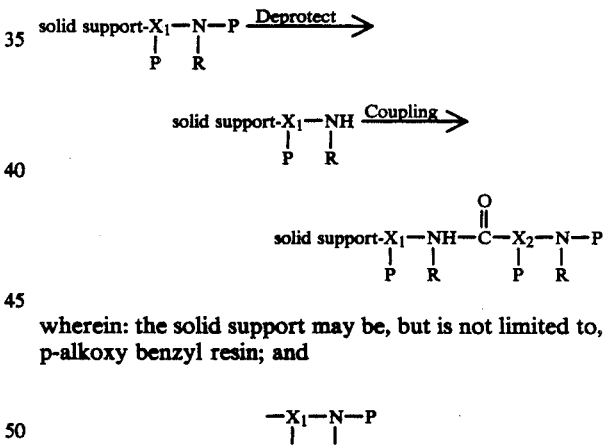

wherein: the solid support may be, but is not limited to, p-alkoxy benzyl resin; and

is an N-protected amino acid.

In the synthetic process of making the desired compound the amino acid derivatives are added one at a time to the insoluble resin until the total sequence has been built up on the resin. The functional groups of the amino acid derivatives are protected by blocking groups to prevent cross reaction during the coupling procedure. These blocking groups include α-tertiary butyloxycarbonyl (BOC), benzyloxycarbonyl (CBZ), benzyl, t-butyl, 9-fluorenylmethyloxycarbonyl (FMOC), 2-(trimethylsilyl)ethyl, and 4-methoxy-2,3,6-trimethylbenzenesulfonyl. Upon completion of the coupling reaction, a functional group is deprotected by standard methods to give an active α-amino function which, in turn, is reacted with a protected amino acid derivative having a free α-carboxyl function thereon.

This procedure is repeated until the desired peptide or pseudopeptide is formed. The compound is then deprotected and removed from the solid support by standard procedures to obtain the final product.

Alternatively, the compounds of the present invention may be prepared in solution, i.e., without using a solid support. In a manner that is similar to the solid phase synthesis the protected amino acid derivatives or analogs are coupled by using standard procedures, then deprotected to yield the desired final compound.

The invention will now be further explained by the following illustrative examples:

EXAMPLE 1

L-Arginyl-L-Aspartyl-L-Valine 1.0 g of N-(9-fluorenylmethyloxycarbonyl)-L-valine p-alkoxybenzyl alcohol resin ester (containing 0.56 mmole of amino acid) is shaken with 20 ml of 20% (v/v) piperidine in methylene chloride for 1 hour to remove the FMOC group. The mixture is filtered and the resin washed with methylene chloride. The deprotected resin is treated with 0.92 g of N-FMOC-L-aspartic acid-$\beta$-t-butyl ester in 15 ml of dimethylformamide in the presence of 0.43 g 1-(3-dimethylaminopropyl)-3-ethylcarbodiimide hydrochloride (EDC), 0.31 ml triethylamine, and 0.30 g 1-hydroxybenzotriazole (HOBT), for 1½ hours. This is filtered, washed with methylene chloride, and the resulting resin treated with 20% piperidine in methylene chloride as above to remove the FMOC group. The resulting resin derivative is then treated as above with 1.36 g N-$\alpha$-FMOC-N-$\omega$-(4-methoxy-2,3,6-trimethylbenzenesulfonyl)-L-arginine in the presence of triethylamine, EDC, and HOBT. The FMOC group is removed as above. The peptide is removed from the resin by treating with 20 ml of 95% trifluoroacetic acid for two hours. The arginine residue is deprotected by overnight treatment with concentrated trifluoroacetic acid. The resulting solution is diluted with 0.5% acetic acid, washed with 3 portions of ethyl acetate, then lyophilized to give L-arginyl-L-aspartyl-L-valine as the ditrifluoroacetate salt; m.p. 90°–95° C.

EXAMPLE 2

L-Arginylglycyl-L-Aspartyl-$\alpha$-Isobutylamide

A. 1.16 g of 1-(3-dimethylaminopropyl)-3-ethylcarbodiimide hydrochloride (EDC) and 0.93 ml of triethylamine are stirred together in 50 ml of methylene chloride for 10 minutes. 2.5 g N-$\alpha$-(FMOC)-L-aspartic acid $\beta$-t-butyl ester, 0.60 ml isobutylamine and 0.82 g hydroxybenzotriazole (HOBT) are added and the solution stirred at room temperature overnight. The solution is diluted with ethyl acetate, washed twice with water and dried over magnesium sulfate. The filtered solution is evaporated in vacuo to give 2.2 g N-$\alpha$-(FMOC)-L-aspartic acid isobutyl amide $\beta$-t-butyl ester.

B. The amide obtained in 2A is dissolved in 20% (v/v) piperidine in methylene chloride and stirred at room temperature for 2 hours. The solution is evaporated in vacuo and the residue dissolved in ethyl acetate and this solution is washed with 10% sodium bicarbonate solution, dried over sodium sulfate, filtered and evaporated to give 1.7 g L-aspartic acid-$\alpha$-isobutyl amide-$\beta$-t-butyl ester.

C. 0.67 g N-FMOC glycine and 0.55 g of the amide obtained in 2B are treated under the conditions of 2A to give N-$\alpha$-(FMOC)-glycyl-L-aspartic acid isobutyl amide-$\beta$-butyl ester.

D. The product obtained in 2C is treated as in 2B to remove the FMOC protecting group to give glycyl-L-aspartic acid isobutyl amide-$\beta$-butyl ester.

E. 0.40 g of the product of 2D and 0.78 g N-$\alpha$-t-BOC-N-$\omega$-(4-methoxy-2,3,6-trimethylbenzenesulfonyl)-L-arginine are treated as in 2A with 0.29 g EDC, 0.17 g HOBT and 0.18 ml triethylamine to give N-$\alpha$-BOC-N-$\omega$-methoxy-2,3,6-trimethylbenzenesulfonyl)-L-arginylglycyl-L-aspartic acid isobutyl amide-$\beta$-butyl ester.

F. 0.35 g of the product obtained in 2E is treated with concentrated trifluoroacetic acid in the presence of two drops of ethanedithiol overnight. The solution is diluted with 0.5% acetic acid and washed with 4×100 ml of ethyl acetate. The aqueous solution was lyophilized to 0.19 g of a white solid, L-arginylglycyl-L-aspartyl-$\alpha$-isobutylamide as the ditrifluoroacetate salt; m.p. 90°–95° C.

EXAMPLE 3

L-Ornithylglycyl-L-Aspartyl-Valine

A. 1.27 g L-valine t-butyl ester and 2.5 g N-$\alpha$-FMOC-L-aspartic acid $\beta$-t-butyl ester are treated as in 2A in the presence of 1.16 g EDC, 0.93 g triethylamine and 0.82 g hydroxybenzotriazole. The resulting product is then deprotected as in 2B to give L-aspartyl-$\beta$-t-butyl ester-L-valine-$\alpha$-t-butyl ester.

B. 1.1 g of the product obtained from 3A is treated with N-$\alpha$-FMOC-glycine in the presence of 0.60 g EDC, and 0.43 g of triethylamine in methylene chloride as in 2A and the resulting product deprotected in 20% piperidine in methylene chloride as in 2B to give 0.65 g glycyl-L-aspartyl-$\beta$-t-butyl ester-L-valine-$\alpha$-t-butyl ester.

C. 0.25 g of the product from 3B is treated with 0.23 g N-$\alpha$-t-BOC-N-$\delta$-CBZ-ornithine in 5 ml of methylene chloride in the presence of 0.12 g EDC, 0.80 g HOBT and 0.09 ml triethylamine as in 2A to give 0.45 g N-$\alpha$-t-BOC-N-$\delta$-CBZ-L-ornithyl-glycyl-L-aspartyl-$\beta$-t-butyl ester-L-valine-$\alpha$-t-butyl ester.

D. The benzyloxycarbonyl protecting group on the product compound of 3C is removed by dissolving 0.45 g of the protected compound in 20 ml of cyclohexene and adding 0.10 g 10% palladium on carbon and heating at reflux, under nitrogen, for 2 hours. The resulting solution is filtered, evaporated, and chromatographed on silica gel in chloroform/methanol/water 90:10:3 to give 0.25 g N-$\alpha$-t-BOC-L-ornithyl-glycyl-L-aspartyl-$\beta$-t-butyl ester-L-valine-$\alpha$-t-butyl ester.

E. 0.23 g of the product obtained in 3D is dissolved in 5 ml trifluoroacetic acid with 3 drops of ethanedithiol added. The solution is stirred for 7 hours, evaporated, and the residue partitioned between ethyl acetate and 0.5M acetic acid. The aqueous portion was separated and lyophilized and the resulting solid purified by HPLC to give L-ornithyl-glycyl-L-aspartyl-L-valine as the ditrifluoroacetate salt; m.p. 122°–25° C.

EXAMPLE 4

L-Arginylsarcosyl-L-Aspartyl-L-Valine

N-$\alpha$-FMOC-sarcosine was substituted for N-$\alpha$-FMOC-glycine and the resulting product was treated with piperidine in methylene chloride as in Example 1 to remove the FMOC group. The corresponding product was obtained. Treating this product with the arginine derivative of Example 1, cleaving the resulting peptide from the resin and deprotecting as in Example 1 gave L-arginylsarcosyl-L-aspartyl-L-valine as the ditrifluoroacetate salt; m.p. 145° C. (dec.).

EXAMPLE 5

L-Arginylglycyl-L-Aspartyl-L-(N-Methyl)Valine

A. 1 g of p-alkoxybenzylalcohol resin (0.5–1 mmole/g of resin), 0.706 g of N-FMOC-N-methyl-L-valine, 0.382 g EDC, 0.270 g HOBT, and 0.28 ml triethylamine are combined in 15 ml of dimethylformamide and shaken for 2 hours. The mixture is filtered and the resin washed with DMF. The resin is treated as above for a second time, then shaken with 0.28 ml glacial acetic acid, 0.955 g EDC, and 0.7 ml triethylamine in DMF and deprotection effected with 20% piperidine in methylene chloride as in 1A. This gives N-Methyl-L-valine-p-alkoxybenzyl resin ester.

B. L-aspartic acid, glycine and L-arginine are coupled and deprotected, sequentially, as in the previous examples and the peptide removed from the resin to give L-arginylglycyl-L-aspartyl-L-(N-methyl)valine as the ditrifluoroacetate salt which decomposes at 153° C.

EXAMPLE 6

L-Arginylglycyl-L-Aspartyl Glycine

Starting with N-FMOC-glycine-p-alkoxy benzyl resin ester, sequentially coupling L-aspartic acid, glycine and arginine, deprotecting and removing the peptide as in the above examples, L-arginylglycyl-L-aspartyl glycine was obtained as the ditrifluoroacetate salt; m.p. 85°–90° C.

EXAMPLE 7

N-(L-Arginyl-2-Aminoethyl)-L-Aspartyl-L-Valine

A. 1.18 g EDC and 0.86 ml of triethylamine are combined in 20 ml of methylene chloride and stirred for 10 minutes. 2.0 g N-$\alpha$-CBZ-L-aspartic acid $\beta$-t-butyl ester, 0.83 g HOBT, 1.30 g L-valine-t-butyl ester and 0.86 ml triethylamine were added and the solution stirred overnight. The solution is diluted with ethyl acetate and washed with 10% citric acid solution, 10% sodium carbonate solution, water, then dried over sodium sulfate, evaporated to give 1.9 g N-$\alpha$-CBZ-L-aspartyl-t-butyl ester-L-valine-t-butyl ester.

B. 2.2 g of N-$\alpha$-CBZ-glycine methyl ester is dissolved in 50 ml of anhydrous toluene and cooled to −78° C., under nitrogen. To this is added 13 ml of 1.5M diisobutyl aluminum hydride in toluene over a period of 1 hour. The solution is stirred for an additional hour at −78° C., then quenched by addition of 50 ml 5% hydrochloric acid solution. The solution is extracted with ethyl acetate which is washed with water and dried over sodium sulfate, evaporated to give 1.55 g N-$\alpha$-CBZ-2-aminoacetaldehyde.

C. The product from 7A is deprotected as in 3D to give L-aspartyl-t-butyl ester-L-valine-t-butyl ester.

D. 1.55 g of the aldehyde from 7B, 3.4 g of the product from 7C, 1.64 g sodium acetate, 1.23 g sodium cyanoborohydride and 1 g of 3 angstrom molecular seives are stirred together in 100 ml methanol for 3 days. The solution is filtered and 5 ml of 5% hydrochloric acid is added. The solution is diluted with water and adjusted to pH 9 with 10% sodium carbonate, then extracted with water, and dried over sodium sulfate. The solution is evaporated and the residue purified by flash chromatograhy in ethyl acetate/hexane, 1:1, to give 1.1 g N-CBZ-aminoethyl-L-aspartyl-$\beta$-t-butyl ester-L-valine-t-butyl ester.

E. The CBZ group is removed from the product of 7D as in 3D to give N-aminoethyl-L-aspartyl-t-butyl ester-L-valine-t-butyl ester.

F. The product from 7E is coupled with N-$\alpha$-t-BOC-N-$\omega$-(4-methoxy-2,3,6-trimethylbenzenesulfonyl)-L-arginine as in 2D and the resulting product deprotected as in 2E to give N-(L-arginyl-2-aminoethyl)-L-aspartyl-L-valine as the tritrifluoroacetate salt; m.p. 91°–5° C.

EXAMPLE 8

L-Arginylglycyl-L-Aspartic Acid $\alpha$-Benzyl Ester

A. 1 g of N-t-BOC-L-aspartic acid $\alpha$-benzyl ester is treated with 0.366 g of 2-(trimethylsilyl)ethanol in the presence of 0.592 g EDC, 0.419 g HOBT and 0.43 ml triethylamine in 20 ml of methylene chloride for 2 hours. The product is isolated as in 2A to give N-t-BOC-L-aspartic acid $\alpha$-benzyl ester-$\beta$-2-(trimethylsilyl)ethyl ester.

B. The product of 8A is deprotected by treating with 10 ml of trifluoroacetic acid in 30 ml of methylene chloride for 2 hours at room temperature. The mixture was cooled to 0° C. and 20 ml of saturated sodium carbonate solution is added dropwise. The layers are separated and the organic layer dried over magnesium sulfate, filtered, evaporated to give L-aspartic acid-$\alpha$-benzyl ester-$\beta$-2-(trimethylsilyl)ethyl ester.

C. The product of 8B and N-t-BOC glycine are coupled in a manner similar to that described in the previous examples to give BOC-glycyl-L-aspartic acid-$\alpha$-benzyl ester-$\beta$-2-(trimethylsilyl)ethyl ester.

D. The BOC group is removed from the product of 8C as in 8B to give glycyl-L-aspartic acid-$\alpha$-benzyl ester-$\beta$-2-(trimethylsilyl)ethyl ester.

E. The product from 8D is coupled to N-$\alpha$-BOC-N-$\omega$-(4-methoxy-2,3,6-trimethylbenzenesulfonyl)-L-arginine as in 2D to give N-$\alpha$-BOC-N-$\omega$(4-methoxy-2,3,6-trimethylbenzenesulfonyl)-L-arginyl-glycylaspartic acid $\alpha$-benzyl ester-$\beta$-2-(trimethylsilyl)ethyl ester.

F. 0.30 g of the product obtained in 8E is stirred with 5 ml of trifluoroacetic acid at room temperature for 24 hours. The reaction mixture is then stirred with 0.5N acetic acid and washed with ethyl acetate. The aqueous layer is lyophilized to give L-arginylglycyl-L-aspartic acid $\alpha$-benzyl ester ditrifluoroacetate; m.p. 85°–7° C.

By using methods analogous to that used in Examples 1 through 8, the following compounds were made:
N-(5-guanidino-2-aminopentyl)glycyl-L-aspartyl-L-valine tritrifluoroacetate; m.p. 90°–95° C.:

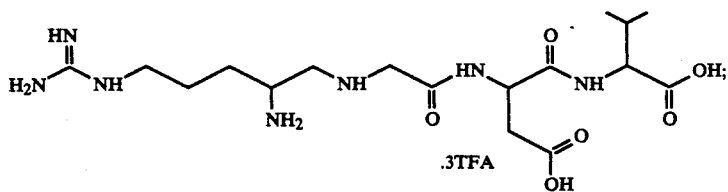

2-[N-(5-guanidinopentanoyl)glycyl-L-aspartyl]-1,2,3,4-tetrahydroisoquinoline:

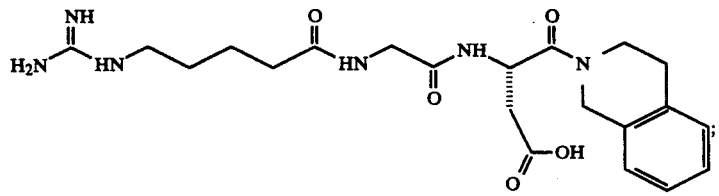

N-(5-guanidinopentanoyl)glycyl-L-aspartylphenethylamide; m.p, 90°-100° C.:

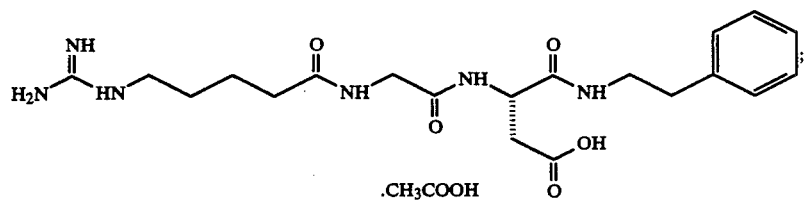

L-arginyl-glycyl-L-N-methylaspartyl-L-valine ditrifluoroacetate:

N-(5-aminopentanoyl)glycyl-L-aspartyl-L-valine trifluoroacetate; m.p. 95°-99° C.:

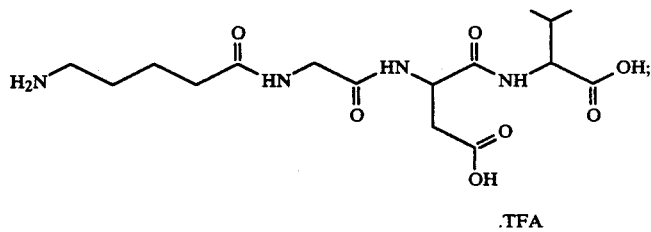

N-(5-guanidinopentanoyl)glycyl-L-aspartyl-L-valine dihydrochloride; m.p. 60°-70° C.:

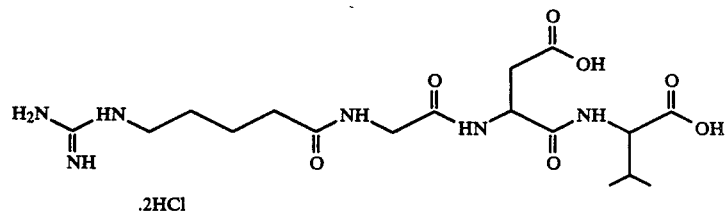

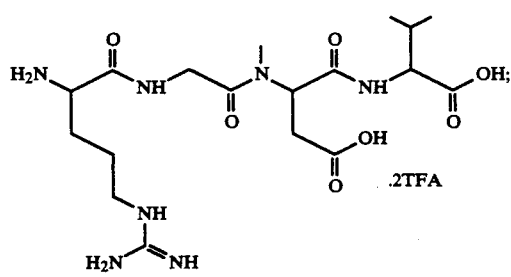

Compounds of the present invention were tested for inhibition of platelet aggregation using the following procedures:

I. Inhibition of Radiolabeled ($^{125}$I) Fibrinogen Binding Assay, which is essentially based on the method described in Proc. Natl. Acad. Sci. USA Vol. 83, pp. 5708-5712, August 1986, and is as follows.

Platelets are washed free of plasma constituents by the albumin density-gradient technique. In each experimental mixture platelets in modified Tyrode's buffer are stimulated with human α-thrombin at 22°–25° C. for 10 minutes (3.125×10" platelets per liter and thrombin at 01 NIH units/ml). Hirudin is then added at a 25-fold excess for 5 minutes before addition of the radiolabeled ligand and any competing ligand. After these additions, the final platelet count in the mixture is 1×10"/liter. After incubation for an additional 30 minutes at 22°–25° C., bound and free ligand are separated by centrifuging 50 μl of the mixture through 300 μl of 20% sucrose at 12,000xg for 4 minutes. The platelet pellet is then separated from the rest of the mixture to determine platelet-bound radioactivity. Nonspecific binding is measured in mixtures containing an excess of unlabeled ligand.

incubated at 37° C. An aliquot of 0.4 ml of platelet suspension was activated by human thrombin at a final concentration of 2 μg/ml of thrombin for one minute. After one minute the reaction was stopped by a thrombin inhibitor. Serial dilution of the compound being tested was then added to the activated platelet, the reaction was allowed to proceed for one minute, followed by the addition of human fibrinogen at a final concentration of 60 μg/ml of fibrinogen. Platelet aggregation was then recorded by an aggregometer. Rate of aggregation was used to calculate $IC_{50}$.

Representative results of platelet aggregation inhibition are shown in Table I.

TABLE I

| | Inhibition of $^{125}$I-Fibrinogen Binding to Platelets $IC_{50}(\mu M)$ | Inhibition of Fibrinogen Mediated Platelet Aggregation | |
|---|---|---|---|
| | | $IC_{50}(\mu M)$ | % Inhibition at 100 μM |
| L-arginyl-L-aspartyl-L-valine | >200 | 100 | 49 |
| L-arginylglycyl-L-aspartyl-α-isobutylamide | 26.5 | 3.6 | 89 |
| L-ornithylglycyl-L-aspartyl-valine | Inhibited <50% at 50 μg/ml | 15 | 80 |
| L-arginylglycyl-L-aspartic acid α-benzyl ester | 25.0 | 14 | 96 |
| L-arginylsarcosyl-L-aspartyl-L-valine | 14 | 14 | 92 |
| L-arginylglycyl-L-aspartyl-L-(N-methyl)-valine | Inhibited <50% at 50 μg/ml | 160 | 30 |
| L-arginylglycyl-L-aspartyl glycine | — | 14.3 | 91 |
| N-(L-arginyl-2-aminoethyl)-L-aspartyl-L-valine | >200 | — | 10 |
| L-arginyl-glycyl-L-N-methylaspartyl-L-valine ditrifluoroacetate | — | >64 | — |
| N-(5-Amino pentanoyl) glycyl-L-aspartyl-L-valine trifluoroacetate | 68.5 | >64 | 67 |
| L-arginyl glycyl-L-aspartyl-α-isobutylamide ditrifluoroacetate | 26.5 | 3.6 | 89 |
| N-δ-L-arginyl-L-ornithyl-L-valine tritrifluoroacetate | — | >100 | 20 |
| L-arginyl-L-aspartyl-L-valine ditrifluoroacetate | >200 | 100 | 49 |
| L-arginyl glycyl glycyl-L-valine ditrifluoroacetate | >200 | >100 | 10 |
| L-arginyl glycyl-L-aspartic acid α-benzyl ester ditrifluoroacetate | 25.0 | 14 | 96 |
| L-ornithyl-glycyl-L-aspartyl-L-valine ditrifluoroacetate | Inhibited <50% at 50 μg/ml | 15 | 80 |
| N-(5-guanidinopentanoyl)glycyl-L-aspartyl-L-valine dihydrochloride | 0.7 | 2.3 | 92 |
| L-arginyl-sarcosyl-L-aspartyl-L-valine ditrifluoroacetate | 14 | 14 | 92 |
| L-arginylglycyl-L-alanyl-L-valine ditrifluoroacetate | Inhibited <50% at 50 μg/ml | >100 | 17.5 |
| L-arginylglycyl-L-aspartyl-L-(N-methyl)-valine ditrifluoroacetate | Inhibited <50% at 50 μg/ml | 160 | 30 |

When binding curves are analyzed by Scatchard analysis, nonspecific binding is derived as a fitted parameter from the binding isotherm by means of a computerized program. To determine the concentration of each inhibitory compound necessary to inhibit 50% of fibrinogen binding to thrombin-stimulated platelets ($IC_{50}$), each compound is tested at 6 or more concentrations with $^{125}$I-labeled fibrinogen held at 0.176 μmol/liter (60 μg/ml). The $IC_{50}$ is derived by plotting residual fibrinogen binding against the logarithm of the sample compound's concentration.

II. Inhibition of Fibrinogen—Mediated Platelet Aggregation, which is essentially based on the method described in Blood, Vol. 66, No. 4, October 1985, pp. 946–952, and is as follows.

Human Platelets were isolated from freshly drawn whole blood and were suspended in 0.14 mol/L NaCl, 2.7 mmol/L K11, 12 mmol/L NaHCO$_3$, 0.42 mmol/L Na$_2$HPO$_4$, 0.55 mmol/L glucose, and 5 mmol/L Hepes, pH 7.35 at 2×10$^8$ platelets/ml. The suspension was The compounds of the present invention may be orally or parenterally administered to mammals. The compounds may be incorporated into pharmaceutical formulations having excipients suitable for these administrations and which do not adversely react with the compounds, for example, water, vegetable oils, certain alcohols and carbohydrates, gelatin and magnesium stearate. The pharmaceutical formulations containing an active compound of the present invention may be made into: tablets, capsules, elixirs, drops or suppositories for enteral administration; and solutions, suspensions or emulsions for parenteral administration.

In general, a compound of this invention is administered in dosages of approximately 1 to 200 mg per dosage unit or higher. The daily dosage is approximately 0.02–5 mg/kg of body weight. It is to be understood, however, that the particular dose for each patient usually depends on very diverse factors, such as the age, body weight, general condition of health, sex, diet and the like of the patient, on the time and route of administration, on the rate of excretion, on the combination of medicaments and on the severity of the disease.

Having described the invention, it will be apparent to one of ordinary skill in the art that changes and modifications can be made thereto without departing from the spirit and scope of the invention as set forth herein.

What is claimed is:

1. A compound of the formula

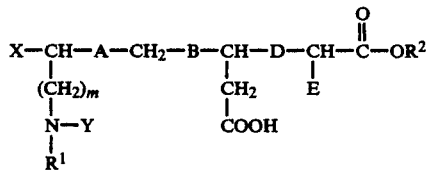

and pharmaceutically acceptable salts thereof wherein:
X is H or

Y is H, alkyl, cycloalkyl, aralkyl or

A, B and D are independently:

E is H, $CH_3$, or

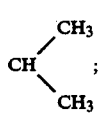

$R^1$ and $R^2$ are independently: H or alkyl; and
m is 2–8;
provided that when X is $NH_2$, then:
m is 3;
E is

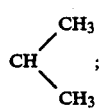

and at least one radical in A, B and D is not

2. A pharmaceutical composition for the prophylaxis or treatment of abnormal thrombus formation in a mammal comprising a pharmaceutically acceptable carrier and a pharmaceutically effective amount of a compound of claim 1.

3. A method of preventing or treating thrombus formation in a mammal comprising the administration of the composition of claim 2.

4. A compound of the formula

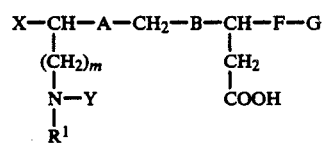

and pharmaceutically acceptable salts thereof wherein:
X is H or

Y is H, alkyl, cycloalkyl, aralkyl or

A and B are independently:

F is

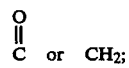

G is $OR^2$,

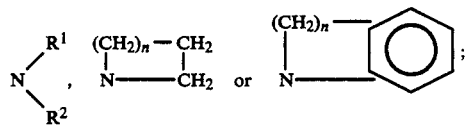

$R^1$ and $R^2$ are independently: H or alkyl;
m is 2–8; and
n is 0–5;
provided that when X is $NH_2$, then:
m is 3;
F is

G is OH; and
that one radical in A and B is not

5. A pharmaceutical composition for the prophylaxis or treatment of abnormal thrombus formulation in a mammal comprising a pharmaceutically acceptable carrier and a pharmaceutically effective amount of a compound of claim 4.

6. A method of preventing or treating thrombus formation in a mammal comprising the administration of the composition of claim 5.

7. L-ornithylglycyl-L-aspartyl-valine.

8. L-arginylsarcosyl-L-aspartyl-L-valine.

9. L-arginylglycyl-L-aspartylglycine.

10. L-arginylglycyl-L-aspartic acid αbenzyl ester.

11. 2-1,2,3,4tetrahydroisoquinoline.

12. N-(5-aminopentanoyl)glycyl-L-aspartyl-L-valine.

* * * * *

UNITED STATES PATENT AND TRADEMARK OFFICE
CERTIFICATE OF CORRECTION

PATENT NO. : 4,952,562
DATED : August 28, 1990
INVENTOR(S) : Scott I. Klein; Bruce F. Molino; Mark Czekaj; Charles J. Gardner; Jeffrey C. Pelletier It is certified that error appears in the above-identified patent and that said Letters Patent is hereby corrected as shown below:

In Claim 11, Column 16, line 3, "2-1,2,3,4 tetrahydroiso-quinoline" should read -- 2-[N-(5-guanidinopentanoyl)glycyl-L-aspartyl]-1,2,3,4-tetrahydroisoquinoline --.

Signed and Sealed this

Twenty-eighth Day of April, 1992

Attest:

HARRY F. MANBECK, JR.

Attesting Officer      Commissioner of Patents and Trademarks